United States Patent
Clayton

(10) Patent No.: US 7,654,264 B2
(45) Date of Patent: Feb. 2, 2010

(54) MEDICAL TUBE INCLUDING AN INFLATABLE CUFF HAVING A NOTCHED COLLAR

(75) Inventor: Jessica Clayton, Campbell, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 626 days.

(21) Appl. No.: 11/488,303

(22) Filed: Jul. 18, 2006

(65) Prior Publication Data

US 2008/0021386 A1    Jan. 24, 2008

(51) Int. Cl.
*A61M 16/00*    (2006.01)
(52) U.S. Cl. .......................... 128/207.15; 128/207.14; 128/200.26
(58) Field of Classification Search ............ 128/207.15, 128/207.14, 200.26, 207.16; 604/101.01, 604/96.01, 102.02
See application file for complete search history.

(56) References Cited

U.S. PATENT DOCUMENTS

| 3,565,079 A | 2/1971 | Jackson ....................... 128/351 |
| 3,659,612 A | 5/1972 | Shiley et al. ................ 128/351 |
| 3,734,100 A | 5/1973 | Walker et al. ............... 128/351 |
| 3,799,173 A * | 3/1974 | Kamen .................. 128/207.15 |
| 3,854,484 A | 12/1974 | Jackson ....................... 128/351 |
| 3,880,168 A | 4/1975 | Berman ....................... 128/351 |
| 3,881,479 A | 5/1975 | Carden .................... 128/145.8 |
| 3,884,242 A | 5/1975 | Bazell et al. ................. 128/351 |
| 3,889,688 A | 6/1975 | Eamkaow ................... 128/351 |
| 4,033,353 A | 7/1977 | La Rosa ..................... 128/351 |
| 4,064,882 A | 12/1977 | Johnson et al. ............. 128/351 |
| 4,091,816 A | 5/1978 | Elam .......................... 128/351 |
| 4,130,617 A | 12/1978 | Wallace ...................... 264/528 |
| 4,134,407 A | 1/1979 | Elam .......................... 128/351 |
| 4,159,722 A | 7/1979 | Walker ....................... 137/496 |
| 4,270,530 A | 6/1981 | Baum et al. ............ 128/204.25 |
| 4,278,081 A | 7/1981 | Jones .................... 128/207.15 |
| 4,289,128 A | 9/1981 | Rüsch ................... 128/207.15 |
| 4,305,392 A | 12/1981 | Chester ...................... 128/276 |
| 4,324,235 A | 4/1982 | Beran .................... 128/207.15 |
| 4,327,720 A | 5/1982 | Bronson et al. ......... 128/207.15 |
| 4,327,721 A | 5/1982 | Goldin et al. .......... 128/207.15 |
| 4,328,056 A | 5/1982 | Snooks ....................... 156/242 |
| 4,341,210 A | 7/1982 | Elam ..................... 128/207.15 |
| 4,378,796 A | 4/1983 | Milhaud ................ 128/207.15 |
| 4,386,179 A | 5/1983 | Sterling ...................... 524/269 |
| 4,446,864 A | 5/1984 | Watson et al. .......... 128/207.14 |
| 4,481,323 A | 11/1984 | Sterling ...................... 524/269 |
| 4,497,318 A | 2/1985 | Donmichael ........... 128/202.28 |

(Continued)

FOREIGN PATENT DOCUMENTS

AU    647206 B2    6/1992

(Continued)

OTHER PUBLICATIONS

International Search Report with Written Opinion, PCT/US2007/073597, 17 pages, Nov. 20, 2007.

*Primary Examiner*—Steven O Douglas

(57) ABSTRACT

A medical device may include a tubular body configured to communicate gas and an inflatable cuff coupled to the tubular body at least by a collar. The tubular body may include an opening. The collar may include a notch positioned relative to the opening in the tubular body such that a passageway extends through at least a portion of the notch and at least a portion of the opening.

27 Claims, 6 Drawing Sheets

U.S. PATENT DOCUMENTS

| | | | |
|---|---|---|---|
| 4,498,473 A | 2/1985 | Gereg | 128/207.15 |
| 4,501,273 A | 2/1985 | McGinnis | 128/207.15 |
| 4,511,354 A | 4/1985 | Sterling | 604/98 |
| 4,552,914 A | 11/1985 | Sterling | 524/269 |
| 4,576,142 A | 3/1986 | Schiff | 128/1 D |
| 4,584,998 A | 4/1986 | McGrail | 128/604 |
| 4,593,690 A | 6/1986 | Sheridan et al. | 128/207.15 |
| 4,607,635 A | 8/1986 | Heyden | 128/207.15 |
| 4,632,108 A | 12/1986 | Geil | 128/207.14 |
| 4,697,573 A | 10/1987 | Schiff | 128/1 D |
| 4,700,700 A | 10/1987 | Eliachar | 128/207.15 |
| 4,762,125 A | 8/1988 | Leiman et al. | 128/207.15 |
| 4,791,923 A | 12/1988 | Shapiro | 125/207.15 |
| 4,793,350 A | 12/1988 | Mar et al. | 128/344 |
| 4,834,087 A | 5/1989 | Coleman et al. | 128/207.14 |
| 4,840,173 A | 6/1989 | Porter, III | 128/207.15 |
| 4,850,348 A | 7/1989 | Pell et al. | 128/207.15 |
| 4,850,371 A | 7/1989 | Broadhurst et al. | 128/719 |
| 4,886,059 A | 12/1989 | Weber | 128/207.15 |
| 4,897,077 A | 1/1990 | Cicciu et al. | 600/18 |
| 4,913,642 A | 4/1990 | Weber | 425/275 |
| 4,924,862 A | 5/1990 | Levinson | 128/207.16 |
| 4,955,375 A | 9/1990 | Martinez | 128/207.15 |
| 4,963,313 A | 10/1990 | Noddin et al. | 264/573 |
| 4,976,261 A | 12/1990 | Gluck et al. | 128/207.15 |
| 4,979,505 A | 12/1990 | Cox | 128/207.15 |
| 4,987,895 A | 1/1991 | Heimlich | 128/207.14 |
| 5,020,534 A | 6/1991 | Pell et al. | 128/207.15 |
| 5,021,045 A | 6/1991 | Buckberg et al. | 604/53 |
| 5,033,466 A | 7/1991 | Weymuller, Jr. | 128/207.15 |
| 5,067,497 A | 11/1991 | Greear et al. | 128/207.15 |
| 5,076,268 A | 12/1991 | Weber | 128/207.15 |
| 5,143,062 A | 9/1992 | Peckham | 128/207.14 |
| 5,201,310 A | 4/1993 | Turnbull | 128/207.15 |
| 5,235,973 A | 8/1993 | Levinson | 128/207.15 |
| 5,241,956 A | 9/1993 | Brain | 128/207.15 |
| 5,251,617 A | 10/1993 | Linder | 128/200.26 |
| 5,251,619 A | 10/1993 | Lee | 128/207.15 |
| 5,273,536 A | 12/1993 | Savas | 604/96 |
| RE34,564 E | 3/1994 | Mar et al. | 604/96 |
| 5,291,882 A | 3/1994 | Makhoul et al. | 128/207.14 |
| 5,305,740 A | 4/1994 | Kolobow | 128/207.14 |
| 5,311,864 A | 5/1994 | Huerta | 128/207.15 |
| 5,322,062 A | 6/1994 | Servas | 128/207.14 |
| 5,334,146 A | 8/1994 | Ozasa | 604/96 |
| 5,338,298 A | 8/1994 | McIntyre | 604/96 |
| 5,372,131 A | 12/1994 | Heinen, Jr. | 128/207.15 |
| 5,405,472 A | 4/1995 | Leone | 156/218 |
| RE34,993 E | 7/1995 | Cicciu et al. | 600/18 |
| 5,443,063 A | 8/1995 | Greenberg | 128/207.15 |
| 5,443,064 A | 8/1995 | Theis et al. | 128/207.15 |
| 5,484,385 A | 1/1996 | Rishton | 600/16 |
| 5,487,383 A | 1/1996 | Levinson | 128/207.15 |
| 5,501,215 A | 3/1996 | Huerta | 128/207.15 |
| 5,503,631 A | 4/1996 | Onishi et al. | 604/96 |
| 5,513,627 A | 5/1996 | Flam | 128/200.26 |
| 5,520,175 A | 5/1996 | Fry | 128/207.15 |
| 5,522,882 A | 6/1996 | Gaterud et al. | 623/1 |
| 5,525,388 A | 6/1996 | Wand et al. | 428/36.9 |
| 5,582,167 A | 12/1996 | Joseph | 128/207.15 |
| 5,632,762 A | 5/1997 | Myler | 606/194 |
| 5,638,813 A | 6/1997 | Augustine | 128/207.15 |
| 5,643,209 A | 7/1997 | Fugoso et al. | 604/96 |
| 5,643,279 A | 7/1997 | Trotta | 606/108 |
| 5,647,848 A | 7/1997 | Jørgensen | 604/96 |
| 5,653,229 A | 8/1997 | Greenberg | 128/207.15 |
| 5,653,230 A | 8/1997 | Ciaglia et al. | 128/207.15 |
| 5,662,608 A | 9/1997 | Imran et al. | 604/96 |
| 5,681,343 A | 10/1997 | Miller | 606/192 |
| 5,695,457 A | 12/1997 | St. Goar et al. | 604/4 |
| 5,697,365 A | 12/1997 | Pell | 128/207.15 |
| 5,702,364 A | 12/1997 | Euteneuer et al. | 604/96 |
| 5,733,299 A | 3/1998 | Sheiban et al. | 606/192 |
| 5,733,301 A | 3/1998 | Forman | 606/192 |
| 5,755,690 A | 5/1998 | Saab | 604/96 |
| 5,779,730 A | 7/1998 | Miller | 606/192 |
| 5,792,172 A | 8/1998 | Fischell et al. | 606/198 |
| 5,797,878 A | 8/1998 | Bleam | 604/196 |
| 5,819,723 A | 10/1998 | Joseph | 128/207.14 |
| 5,819,733 A | 10/1998 | Bertram | 128/207.15 |
| 5,830,182 A | 11/1998 | Wang et al. | 604/96 |
| 5,830,227 A | 11/1998 | Fischell et al. | 606/194 |
| 5,832,920 A | 11/1998 | Field | 128/207.14 |
| 5,865,721 A | 2/1999 | Andrews et al. | 600/18 |
| 5,879,282 A | 3/1999 | Fischell et al. | 600/3 |
| 5,879,369 A | 3/1999 | Ishida | 606/194 |
| 5,881,726 A | 3/1999 | Neame | 128/207.15 |
| 5,891,386 A | 4/1999 | Deitermann et al. | 264/526 |
| 5,896,858 A | 4/1999 | Brain | 128/207.15 |
| 5,913,861 A | 6/1999 | Trotta | 606/108 |
| 5,947,925 A | 9/1999 | Ashiya et al. | 604/96 |
| 5,951,497 A | 9/1999 | Wallace et al. | 600/587 |
| 5,954,636 A | 9/1999 | Schwartz et al. | 600/120 |
| 5,972,441 A | 10/1999 | Campbell et al. | 428/34.1 |
| 5,988,167 A | 11/1999 | Kamen | 128/207.15 |
| 5,996,582 A | 12/1999 | Turnbull | 128/207.29 |
| 6,004,289 A | 12/1999 | Saab | 604/96 |
| 6,021,779 A | 2/2000 | Pagan | 128/207.15 |
| 6,055,984 A | 5/2000 | Brain | 128/207.14 |
| 6,062,223 A | 5/2000 | Palazzo et al. | 128/207.15 |
| 6,095,144 A | 8/2000 | Pagan | 128/207.15 |
| 6,129,737 A | 10/2000 | Hamilton et al. | 606/194 |
| 6,135,111 A | 10/2000 | Mongeon | 128/207.15 |
| 6,190,393 B1 | 2/2001 | Bevier et al. | 606/108 |
| 6,196,225 B1 | 3/2001 | Allgeyer | 128/207.15 |
| 6,200,325 B1 | 3/2001 | Durcan et al. | 606/108 |
| 6,210,364 B1 | 4/2001 | Anderson et al. | 604/96.01 |
| 6,224,803 B1 | 5/2001 | Tiernan | 264/166 |
| 6,228,072 B1 | 5/2001 | Omaleki et al. | 604/529 |
| 6,238,382 B1 | 5/2001 | Schock et al. | 604/533 |
| 6,251,094 B1 | 6/2001 | Bleam | 604/96.01 |
| 6,258,108 B1 | 7/2001 | Lary | 606/159 |
| 6,264,679 B1 | 7/2001 | Keller et al. | 607/105 |
| 6,270,521 B1 | 8/2001 | Fischell et al. | 623/1.11 |
| 6,273,878 B1 | 8/2001 | Muni | 604/265 |
| 6,273,910 B1 | 8/2001 | Limon | 623/1.15 |
| 6,280,423 B1 | 8/2001 | Davey et al. | 604/264 |
| 6,287,506 B1 | 9/2001 | Hudgins et al. | 264/515 |
| 6,293,959 B1 | 9/2001 | Miller et al. | 606/194 |
| 6,321,749 B1 | 11/2001 | Toti et al. | 128/207.14 |
| 6,346,092 B1 | 2/2002 | Leschinsky | 604/96.01 |
| 6,379,365 B1 | 4/2002 | Diaz | 606/108 |
| 6,382,209 B1 | 5/2002 | Toye | 128/207.14 |
| 6,383,212 B2 | 5/2002 | Durcan et al. | 623/1.11 |
| 6,386,199 B1 | 5/2002 | Alfery | 128/207.15 |
| 6,390,093 B1 | 5/2002 | Mongeon | 128/207.15 |
| 6,391,002 B1 | 5/2002 | Kokish | 604/96.01 |
| 6,394,978 B1 | 5/2002 | Boyle et al. | 604/103.06 |
| 6,406,457 B1 | 6/2002 | Wang et al. | 604/96.01 |
| 6,439,232 B1 | 8/2002 | Brain | 128/207.15 |
| 6,458,313 B2 | 10/2002 | Hudgins et al. | 264/515 |
| 6,460,540 B1 | 10/2002 | Klepper | 128/207.14 |
| 6,464,718 B1 | 10/2002 | Miller et al. | 623/1.11 |
| 6,482,171 B1 | 11/2002 | Corvi et al. | 604/96.01 |
| 6,491,711 B1 | 12/2002 | Durcan | 606/194 |
| 6,497,678 B2 | 12/2002 | Schock | 604/103.06 |
| 6,526,977 B1 | 3/2003 | Göbel | 128/207.14 |
| 6,544,223 B1 | 4/2003 | Kokish | 604/103.01 |
| 6,544,224 B1 | 4/2003 | Steese-Bradley | 604/103.06 |
| 6,572,813 B1 | 6/2003 | Zhang et al. | 264/519 |
| 6,575,934 B2 | 6/2003 | Duchamp | 604/102.02 |
| 6,595,966 B2 | 7/2003 | Davey et al. | 604/264 |
| 6,605,031 B1 | 8/2003 | Mourtada et al. | 600/3 |
| 6,609,521 B1 | 8/2003 | Belani et al. | 128/207.14 |

| | | | | |
|---|---|---|---|---|
| 6,638,245 B2 | 10/2003 | Miller et al. .............. 604/96.01 |
| 6,641,694 B1 | 11/2003 | Lee ....................... 156/244.14 |
| 6,651,664 B1 | 11/2003 | Lomholt ................. 128/207.14 |
| 6,652,568 B1 | 11/2003 | Becker et al. .............. 623/1.11 |
| 6,663,614 B1 | 12/2003 | Carter ....................... 604/525 |
| 6,692,511 B2 | 2/2004 | Tiernan ...................... 606/194 |
| 6,698,428 B2 | 3/2004 | Brain ..................... 128/207.14 |
| 6,702,782 B2 | 3/2004 | Miller et al. .............. 604/96.01 |
| 6,705,318 B1 | 3/2004 | Brain ..................... 128/207.14 |
| 6,722,368 B1 | 4/2004 | Shaikh .................... 128/207.15 |
| 6,725,862 B2 | 4/2004 | Klinberg et al. ......... 128/207.14 |
| 6,729,325 B2 | 5/2004 | Alfery ................... 128/200.26 |
| 6,745,773 B1 | 6/2004 | Gobel .................... 128/207.15 |
| 6,746,424 B2 | 6/2004 | Stamberg ............... 604/103.06 |
| 6,790,222 B2 | 9/2004 | Kugler et al. .............. 623/1.11 |
| 6,792,943 B2 | 9/2004 | Kumar et al. ........... 128/200.26 |
| 6,796,309 B2 | 9/2004 | Nash et al. .............. 128/207.14 |
| 6,799,574 B1 | 10/2004 | Collins ................... 128/207.15 |
| 6,802,317 B2 | 10/2004 | Göbel .................... 128/207.14 |
| 6,830,049 B2 | 12/2004 | Augustine et al. ....... 128/207.15 |
| 6,830,559 B2 | 12/2004 | Schock .................. 604/103.06 |
| 6,863,678 B2 | 3/2005 | Lee et al. .................. 606/192 |
| 6,887,267 B2 | 5/2005 | Dworschak et al. ......... 623/1.23 |
| 6,913,601 B2 | 7/2005 | St. Goar et al. .............. 604/509 |
| 6,942,640 B2 | 9/2005 | Kokish .................. 604/96.01 |
| 6,951,566 B2 | 10/2005 | Lary .......................... 606/159 |
| 6,960,222 B2 | 11/2005 | Vo et al. ..................... 606/200 |
| 6,966,890 B2 | 11/2005 | Coyle et al. ............. 604/103.04 |
| 7,201,168 B2 * | 4/2007 | McGrail et al. ......... 128/207.14 |
| 2001/0000350 A1 | 4/2001 | Durcan et al. .............. 623/1.11 |
| 2001/0001957 A1 | 5/2001 | Allgeyer ................. 128/207.15 |
| 2001/0004703 A1 | 6/2001 | Tiernan ...................... 606/194 |
| 2001/0013345 A1 | 8/2001 | Bertram ................. 128/200.26 |
| 2001/0016705 A1 | 8/2001 | Omaleki et al. ......... 604/103.06 |
| 2001/0018917 A1 | 9/2001 | Brain ..................... 128/207.14 |
| 2001/0023334 A1 | 9/2001 | St. Goar et al. ......... 604/101.04 |
| 2001/0037808 A1 | 11/2001 | Deem et al. ............. 128/200.24 |
| 2001/0044644 A1 | 11/2001 | Keller et al. .................. 607/105 |
| 2001/0052660 A1 | 12/2001 | Hudgins et al. .............. 264/515 |
| 2001/0054425 A1 | 12/2001 | Bertram ................. 128/207.15 |
| 2002/0068953 A1 | 6/2002 | Kokish ....................... 606/194 |
| 2002/0074339 A1 * | 6/2002 | Gilmore ........................ 221/2 |
| 2002/0078962 A1 | 6/2002 | Nash et al. .............. 128/207.15 |
| 2002/0082553 A1 | 6/2002 | Duchamp ............... 604/103.06 |
| 2002/0103455 A1 | 8/2002 | Zhang et al. .............. 604/96.01 |
| 2002/0132072 A1 | 9/2002 | Wang et al. ................. 428/35.2 |
| 2002/0198491 A1 | 12/2002 | Miller et al. .............. 604/96.01 |
| 2002/0198492 A1 | 12/2002 | Miller et al. .............. 604/96.01 |
| 2003/0000534 A1 | 1/2003 | Alfery ................... 128/207.14 |
| 2003/0014008 A1 | 1/2003 | Jacques .................. 604/96.01 |
| 2003/0055447 A1 | 3/2003 | Lee et al. ..................... 606/191 |
| 2003/0060832 A1 | 3/2003 | Guinan et al. ............... 606/108 |
| 2003/0062049 A1 | 4/2003 | Kolobow ................. 128/207.14 |
| 2003/0066532 A1 | 4/2003 | Gobel .................... 128/207.15 |
| 2003/0100915 A1 | 5/2003 | Quint ........................ 606/194 |
| 2003/0105508 A1 | 6/2003 | Johnson et al. ............. 623/1.11 |
| 2003/0120206 A1 | 6/2003 | Cartledge et al. ....... 604/102.03 |
| 2003/0136413 A1 | 7/2003 | Brain et al. .............. 128/207.14 |
| 2003/0139703 A1 | 7/2003 | Burkett et al. ............ 604/96.01 |
| 2003/0139760 A1 | 7/2003 | Stamberg .................. 606/194 |
| 2003/0144677 A1 | 7/2003 | Lary .......................... 606/159 |
| 2003/0150461 A1 | 8/2003 | Dhuper et al. ........... 128/207.14 |
| 2003/0192548 A1 | 10/2003 | Chang ................... 128/207.14 |
| 2003/0213492 A1 | 11/2003 | Alfery et al. ............. 128/207.14 |
| 2003/0226566 A1 | 12/2003 | Dhuper et al. ........... 128/207.15 |
| 2003/0230590 A1 * | 12/2003 | Gilmore ........................ 221/2 |
| 2004/0020491 A1 | 2/2004 | Fortuna .................. 128/207.15 |
| 2004/0068287 A1 | 4/2004 | Lim et al. .................... 606/194 |
| 2004/0079376 A1 | 4/2004 | Melker .................. 128/207.14 |
| 2004/0143240 A1 | 7/2004 | Armstrong et al. ............ 604/528 |
| 2004/0154623 A1 | 8/2004 | Schaeffer et al. ........ 128/207.14 |
| 2004/0167593 A1 | 8/2004 | Keller et al. .................. 607/105 |
| 2004/0182384 A1 | 9/2004 | Alfery ................... 128/200.26 |
| 2004/0186461 A1 | 9/2004 | DiMatteo .................... 604/539 |
| 2004/0187872 A1 | 9/2004 | Brain .................... 128/207.14 |
| 2004/0199086 A1 | 10/2004 | Crisp .......................... 600/581 |
| 2004/0200479 A1 | 10/2004 | Chang ................... 128/207.14 |
| 2004/0255951 A1 | 12/2004 | Grey ..................... 128/207.14 |
| 2004/0255954 A1 | 12/2004 | Zgoda et al. ............. 128/207.29 |
| 2004/0267197 A1 | 12/2004 | Blankenship .......... 604/103.06 |
| 2004/0267280 A1 | 12/2004 | Nishide et al. .............. 606/108 |
| 2005/0008806 A1 | 1/2005 | Schewe et al. ............. 428/36.9 |
| 2005/0075662 A1 | 4/2005 | Pedersen et al. ............ 606/194 |
| 2005/0081861 A1 | 4/2005 | Nasir .................... 128/207.14 |
| 2005/0090846 A1 | 4/2005 | Pedersen et al. ............ 606/159 |
| 2005/0123640 A1 | 6/2005 | Mahoney et al. ............ 425/392 |
| 2005/0166926 A1 | 8/2005 | Nomori .................. 128/207.15 |
| 2005/0199244 A1 | 9/2005 | Tateo et al. ............. 128/207.15 |
| 2005/0229933 A1 | 10/2005 | McGrail et al. ........ 128/207.15 |
| 2005/0240213 A1 | 10/2005 | Lee et al. ..................... 606/194 |
| 2005/0274382 A1 | 12/2005 | Lomholt ................. 128/207.15 |
| 2005/0284482 A1 | 12/2005 | Patel ..................... 128/207.14 |
| 2005/0284483 A1 | 12/2005 | Patel ..................... 128/207.14 |

FOREIGN PATENT DOCUMENTS

| | | |
|---|---|---|
| AU | 8792591 A | 6/1992 |
| CA | 2056013 A1 | 6/1992 |
| CA | 2056013 C | 6/1992 |
| DE | 3406294 | 5/1985 |
| DE | 69102982D | 8/1994 |
| DE | 69102982 T | 10/1994 |
| DK | 489507 T | 9/1994 |
| EP | 0010880 B1 | 2/1984 |
| EP | 0064701 B1 | 7/1986 |
| EP | 0274130 A2 | 7/1988 |
| EP | 0274411 A2 | 7/1988 |
| EP | 0274411 A3 | 7/1988 |
| EP | 0279958 A1 | 8/1988 |
| EP | 0335205 A1 | 10/1989 |
| EP | 0150960 B1 | 1/1990 |
| EP | 0152694 B1 | 4/1990 |
| EP | 0374859 A1 | 6/1990 |
| EP | 0378151 A2 | 7/1990 |
| EP | 0378151 A3 | 7/1990 |
| EP | 0428976 A1 | 5/1991 |
| EP | 0489507 A1 | 6/1992 |
| EP | 0429523 B1 | 8/1992 |
| EP | 0351734 B1 | 9/1992 |
| EP | 0266957 B1 | 12/1992 |
| EP | 0318919 B1 | 1/1994 |
| EP | 0420486 B1 | 4/1994 |
| EP | 0592885 A2 | 4/1994 |
| EP | 0592885 A3 | 4/1994 |
| EP | 0351687 B1 | 6/1994 |
| EP | 0489507 B1 | 7/1994 |
| EP | 0414350 B1 | 8/1994 |
| EP | 0407663 B1 | 12/1994 |
| EP | 0658356 A2 | 6/1995 |
| EP | 0658356 A3 | 6/1995 |
| EP | 0347101 B1 | 7/1995 |
| EP | 0355937 B1 | 11/1995 |
| EP | 0383429 B1 | 11/1995 |
| EP | 0707864 A1 | 4/1996 |
| EP | 0485903 B1 | 10/1996 |
| EP | 0457456 B1 | 12/1996 |
| EP | 0606164 B1 | 12/1996 |
| EP | 0471029 B1 | 1/1997 |
| EP | 0514400 B1 | 3/1997 |
| EP | 0409929 B1 | 4/1997 |
| EP | 0768097 A2 | 4/1997 |
| EP | 0566684 B1 | 6/1997 |
| EP | 0768097 A3 | 7/1997 |
| EP | 0783897 A2 | 7/1997 |
| EP | 0784989 A2 | 7/1997 |
| EP | 0795340 A2 | 9/1997 |

| | | | | | | |
|---|---|---|---|---|---|---|
| EP | 0796633 | A1 | 9/1997 | EP | 0304258 A2 | 9/2004 |
| EP | 0351687 | B2 | 10/1997 | EP | 0304258 A3 | 9/2004 |
| EP | 0819413 | A2 | 1/1998 | EP | 0850605 B1 | 9/2004 |
| EP | 0795340 | A3 | 3/1998 | EP | 1000593 B1 | 9/2004 |
| EP | 0784989 | A3 | 4/1998 | EP | 1210135 B1 | 10/2004 |
| EP | 0836860 | A2 | 4/1998 | EP | 0819413 B1 | 12/2004 |
| EP | 0841071 | A3 | 4/1998 | EP | 1023913 B1 | 12/2004 |
| EP | 0841071 | A2 | 5/1998 | EP | 1488822 A2 | 12/2004 |
| EP | 0669114 | B1 | 6/1998 | EP | 11320598 B1 | 3/2005 |
| EP | 0274130 | A3 | 7/1998 | EP | 1000591 B1 | 4/2005 |
| EP | 0850605 | A2 | 7/1998 | EP | 1107801 B1 | 5/2005 |
| EP | 0853957 | A2 | 7/1998 | EP | 1488822 A3 | 5/2005 |
| EP | 0675743 | B1 | 9/1998 | EP | 1557193 A2 | 7/2005 |
| EP | 0836860 | A3 | 9/1998 | EP | 1252909 B1 | 9/2005 |
| EP | 0850605 | A3 | 9/1998 | EP | 1056501 B1 | 11/2005 |
| EP | 0980278 | B1 | 9/1998 | EP | 1267981 B1 | 11/2005 |
| EP | 0868927 | A1 | 10/1998 | EP | 1557193 A3 | 11/2005 |
| EP | 0872253 | | 10/1998 | EP | 0707864 B1 | 12/2005 |
| EP | 0853957 | A3 | 11/1998 | ES | 2057782 T | 10/1994 |
| EP | 0875263 | A2 | 11/1998 | GB | 1313347 | 7/1970 |
| EP | 0876805 | A2 | 11/1998 | GB | 2033759 A | 10/1979 |
| EP | 0592320 | B1 | 12/1998 | GB | 2174303 A | 11/1986 |
| EP | 0776226 | B1 | 12/1998 | GB | 2250440 A | 11/1991 |
| EP | 0884061 | A2 | 12/1998 | GB | 2250440 B | 10/1994 |
| EP | 0634943 | B1 | 3/1999 | GB | 2298580 A | 9/1996 |
| EP | 0556309 | B1 | 4/1999 | GB | 2324735 A | 11/1998 |
| EP | 0884061 | A3 | 4/1999 | GB | 2328615 A | 3/1999 |
| EP | 0819413 | A3 | 7/1999 | GB | 2344528 A | 6/2000 |
| EP | 0783897 | A3 | 8/1999 | IE | 64695 B1 | 11/1991 |
| EP | 0701460 | B1 | 9/1999 | IE | 913956 A | 6/1992 |
| EP | 1000591 | A2 | 5/2000 | IL | 100025 A | 12/1995 |
| EP | 1000592 | A2 | 5/2000 | IL | 100025D | 12/1995 |
| EP | 1000593 | A2 | 5/2000 | JP | 3241770 | 9/1992 |
| EP | 1000591 | A3 | 6/2000 | JP | 3241770 B2 | 9/1992 |
| EP | 1000593 | A3 | 6/2000 | JP | 4272766 A | 9/1992 |
| EP | 1005877 | A2 | 7/2000 | WO | 8001647 A1 | 8/1980 |
| EP | 1005877 | A3 | 8/2000 | WO | 8606285 A1 | 11/1986 |
| EP | 1023913 | A1 | 8/2000 | WO | 8907958 A1 | 9/1989 |
| EP | 0669142 | B1 | 9/2000 | WO | 8908472 A1 | 9/1989 |
| EP | 0829238 | B1 | 9/2000 | WO | 8912425 A1 | 12/1989 |
| EP | 1000592 | A3 | 11/2000 | WO | 9005554 A2 | 5/1990 |
| EP | 0861104 | B1 | 12/2000 | WO | 9117788 A1 | 11/1991 |
| EP | 1132059 | A1 | 9/2001 | WO | 9200697 A1 | 1/1992 |
| EP | 0705116 | B1 | 4/2002 | WO | 9203095 A1 | 3/1992 |
| EP | 0836503 | B1 | 5/2002 | WO | 9203178 A1 | 3/1992 |
| EP | 1219317 | A2 | 7/2002 | WO | 9207602 | 5/1992 |
| EP | 1226798 | A2 | 7/2002 | WO | 9218195 A1 | 10/1992 |
| EP | 1252909 | A2 | 10/2002 | WO | 9220280 A1 | 11/1992 |
| EP | 0876805 | A3 | 1/2003 | WO | 9324170 A1 | 12/1993 |
| EP | 1252909 | A3 | 1/2003 | WO | 9414493 A1 | 7/1994 |
| EP | 0932376 | B1 | 2/2003 | WO | 9425098 A1 | 11/1994 |
| EP | 1293178 | A2 | 3/2003 | WO | 9523619 A1 | 9/1995 |
| EP | 0930909 | B1 | 5/2003 | WO | 9523625 A1 | 9/1995 |
| EP | 0796633 | B1 | 7/2003 | WO | 9525560 A1 | 9/1995 |
| EP | 0768904 | B1 | 9/2003 | WO | 9607445 A1 | 3/1996 |
| EP | 1340517 | A2 | 9/2003 | WO | 9612455 A1 | 5/1996 |
| EP | 1346748 | A1 | 9/2003 | WO | 96/37250 A1 | 11/1996 |
| EP | 0795340 | B1 | 12/2003 | WO | 9637250 A1 | 11/1996 |
| EP | 1226798 | A3 | 12/2003 | WO | 9638109 A1 | 12/1996 |
| EP | 1219317 | A3 | 1/2004 | WO | 9640340 A2 | 12/1996 |
| EP | 1293178 | A3 | 1/2004 | WO | 9640340 A3 | 12/1996 |
| EP | 1374943 | A1 | 1/2004 | WO | 9712640 | 4/1997 |
| EP | 0875263 | B1 | 2/2004 | WO | 9712641 A1 | 4/1997 |
| EP | 1340517 | A3 | 2/2004 | WO | 9722378 A1 | 6/1997 |
| EP | 1398131 | A1 | 3/2004 | WO | 9726040 | 7/1997 |
| EP | 1200018 | B1 | 5/2004 | WO | 9732620 | 9/1997 |
| EP | 0784989 | B1 | 6/2004 | WO | 9807388 A1 | 2/1998 |
| EP | 0853957 | B1 | 6/2004 | WO | 9831415 A1 | 7/1998 |
| EP | 1061984 | B1 | 6/2004 | WO | 9837833 A1 | 9/1998 |
| EP | 1430925 | A1 | 6/2004 | WO | 9932182 | 7/1999 |
| EP | 0783897 | B1 | 7/2004 | WO | 9938548 | 8/1999 |
| EP | 0868927 | B1 | 7/2004 | WO | 9942164 A1 | 8/1999 |
| EP | 1438989 | A2 | 7/2004 | WO | 9945991 | 9/1999 |

| | | | | | | |
|---|---|---|---|---|---|---|
| WO | 9966975 | | 12/1999 | WO | 03028795 A1 | 4/2003 |
| WO | 0002613 | A1 | 1/2000 | WO | 03030975 A2 | 4/2003 |
| WO | 0009180 | A2 | 2/2000 | WO | 03030975 A3 | 4/2003 |
| WO | 0009180 | A3 | 2/2000 | WO | 03/061747 A1 | 7/2003 |
| WO | 0018461 | A1 | 4/2000 | WO | 03061747 A1 | 7/2003 |
| WO | 0035358 | A1 | 6/2000 | WO | 03/097144 A1 | 11/2003 |
| WO | 0053122 | A1 | 9/2000 | WO | 03101516 | 12/2003 |
| WO | 0057945 | A2 | 10/2000 | WO | 2004060467 A1 | 7/2004 |
| WO | 0057945 | A3 | 10/2000 | WO | 2004064892 A2 | 8/2004 |
| WO | 0062849 | | 10/2000 | WO | 2004064892 A3 | 8/2004 |
| WO | 0062849 | A1 | 10/2000 | WO | 2004066809 A2 | 8/2004 |
| WO | 0113809 | A1 | 3/2001 | WO | 2004066809 A3 | 8/2004 |
| WO | 0113976 | A1 | 3/2001 | WO | 2004069316 A2 | 8/2004 |
| WO | 0121245 | A1 | 3/2001 | WO | 2004069316 A3 | 8/2004 |
| WO | 0134221 | A2 | 5/2001 | WO | 2004082754 A1 | 9/2004 |
| WO | 0134221 | A3 | 5/2001 | WO | 2004089453 A2 | 10/2004 |
| WO | 0156641 | A1 | 8/2001 | WO | 2004089453 A3 | 10/2004 |
| WO | 0185229 | A2 | 11/2001 | WO | 2004101046 A1 | 11/2004 |
| WO | 0185247 | A1 | 11/2001 | WO | 2004101047 A1 | 11/2004 |
| WO | 0241934 | A2 | 5/2002 | WO | 2005007219 A2 | 1/2005 |
| WO | 0241934 | A3 | 5/2002 | WO | 2005007230 A2 | 1/2005 |
| WO | 02072170 | A2 | 9/2002 | WO | 2005007230 A3 | 1/2005 |
| WO | 02072170 | A3 | 9/2002 | WO | 2005009526 A1 | 2/2005 |
| WO | 000334 | A1 | 1/2003 | WO | 2005023358 A1 | 3/2005 |
| WO | 03000334 | A1 | 1/2003 | WO | 2005060843 A1 | 7/2005 |
| WO | 03024498 | A1 | 3/2003 | WO | 2005094926 A1 | 10/2005 |
| WO | 03026534 | A1 | 4/2003 | WO | 2005112796 A2 | 12/2005 |
| WO | 03028614 | A2 | 4/2003 | WO | 2005118039 A1 | 12/2005 |
| WO | 03028614 | A3 | 4/2003 | | | |

* cited by examiner

_US 7,654,264 B2_

MEDICAL TUBE INCLUDING AN INFLATABLE CUFF HAVING A NOTCHED COLLAR

TECHNICAL FIELD

The present disclosure relates generally to the field of medical devices, e.g., a medical tube including an inflatable cuff having a notched collar.

BACKGROUND

Conventional methods of endotracheal intubation involve the insertion of a tubular device, e.g., an endotracheal tube, into the trachea. The endotracheal tube typically passes through the trachea and terminates above the carina, allowing gases to be directed through the tube and into the lungs.

A primary objective of this type of treatment is the mechanical ventilation of a subject's lungs, which may be required or appropriate due to the subject's medical condition. In order to create the air pressure necessary to artificially ventilate the lungs, the passageways around the tube are typically sealed, which may be accomplished, e.g., using an inflatable cuff provided around the tube. With the tube in place, the cuff is typically located within the trachea about 3-5 centimeters above the carina. The cuff may then be inflated to expand and seal against the wall of the trachea, thereby preventing gases being pumped into the lungs from backing up around the tube.

Although this method of treatment has been relatively successful, problems remain. For example, with cuffed endotracheal tubes, secretions may collect proximate the cuff, providing a site for the possible accumulation of pathogens. Various methods have been devised for removing such secretions. For example, a small opening may be provided above the cuff with an associated suction lumen. Fluids and/or solids (e.g., secretions) can be periodically or continuously removed through the opening and lumen by suction.

SUMMARY

In accordance with one embodiment of the present disclosure, a medical device may include a tubular body configured to communicate gas and an inflatable cuff coupled to the tubular body at least by a collar. The tubular body may include an opening and the collar may include a notch positioned relative to the opening such that a passageway extends through at least a portion of the notch and at least a portion of the opening.

In accordance with another embodiment of the present disclosure, a method of attaching an inflatable cuff to a tubular body of a medical tube may be provided. The method may include forming a notch in a collar of an inflatable cuff, mounting the inflatable cuff on a tubular body having an opening, and positioning the notch in the collar relative to the opening in the tubular body such that a passageway extends through at least a portion of the notch and at least a portion of the opening.

In accordance with another embodiment of the present disclosure, a method of attaching an inflatable cuff having a collar to a tubular body of a medical tube is provided. The method may include mounting the inflatable cuff on the tubular body, and forming a notch in the collar of the mounted cuff.

In accordance with another embodiment of the present disclosure, a medical device may include conveying means for channeling gas to an area of the body, sealing means for sealing said conveying means against the wall of a body cavity, and attaching means for attaching said sealing means to said conveying means, wherein the attaching means includes a collar having a notch.

In accordance with another embodiment of the present disclosure, a method for intubation may be provided. The method may include inserting a tube into the body cavity, wherein the tube includes an inflatable cuff coupled to a tubular body at least by a collar, the collar including a notch positioned relative to an opening in the tubular body such that a passageway extends through at least a portion of the notch and at least a portion of the opening. The method may further include inflating the cuff within a body cavity and conveying gas to an area of the body through the tubular body.

DETAILED DESCRIPTION OF THE DRAWING

Selected embodiments of the disclosure may be understood by reference, in part, to FIGS. 1-9, wherein like numbers refer to same and like parts. The present disclosure is broadly concerned with medical tubes (e.g., endotracheal, tracheostomy, or oropharyngeal tubes or other tubes or catheters) adapted to be intubated into one or more passageways (e.g., the trachea and/or pharynx) of a subject in connection with a medical procedure. For example, certain embodiments are directed toward endotracheal tubes inserted into a subject's trachea to facilitate mechanical ventilation of the subject's lungs. Certain embodiments include tubes having an improved configuration for periodic removal of fluids and/or solids that collect adjacent an inflatable cuff used to seal, secure and/or position the tube against the tracheal wall. The inflatable cuff may include a notched collar, which may be advantageous or desirable. As used throughout this document, the term "subject" may include any human or other animal.

Figure 1:
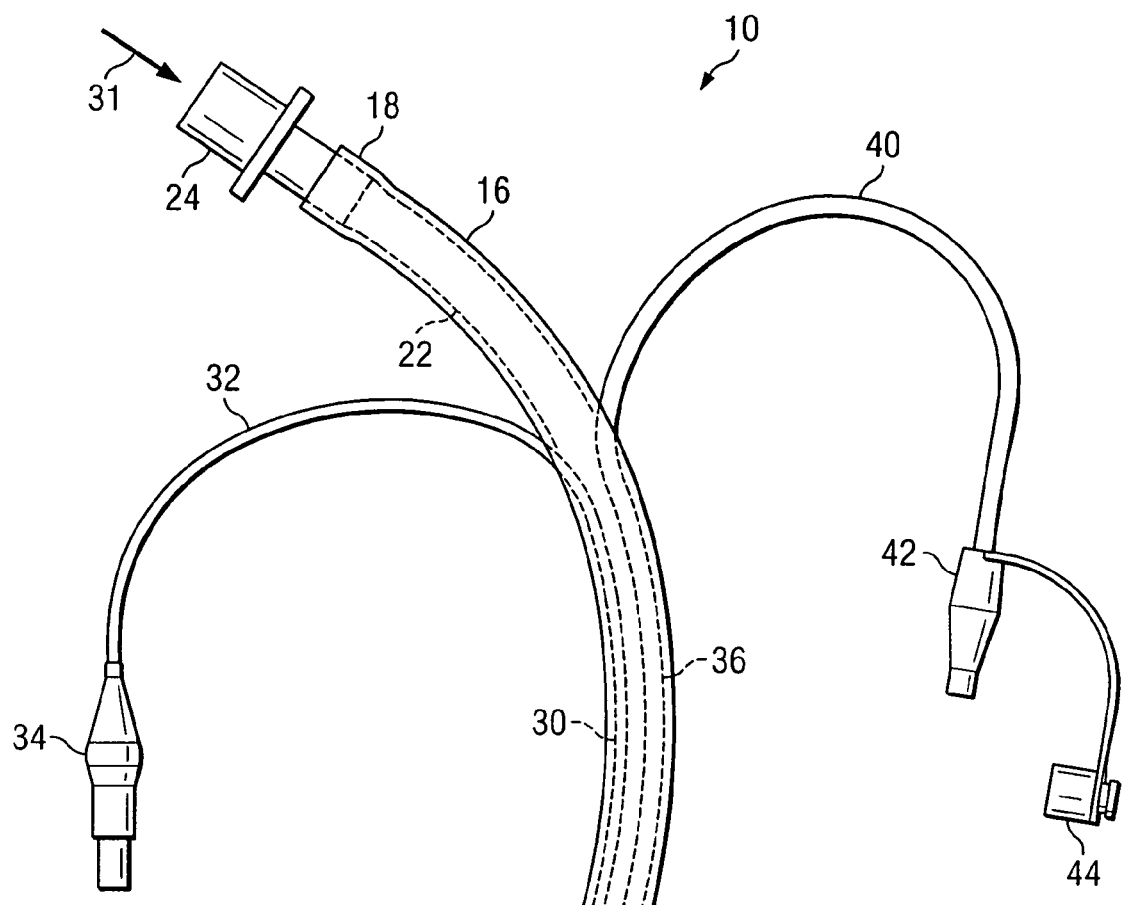
FIG. 1 illustrates a medical tube including an inflatable cuff having a notched collar, in accordance with an example embodiment of the disclosure.
Figure 1:
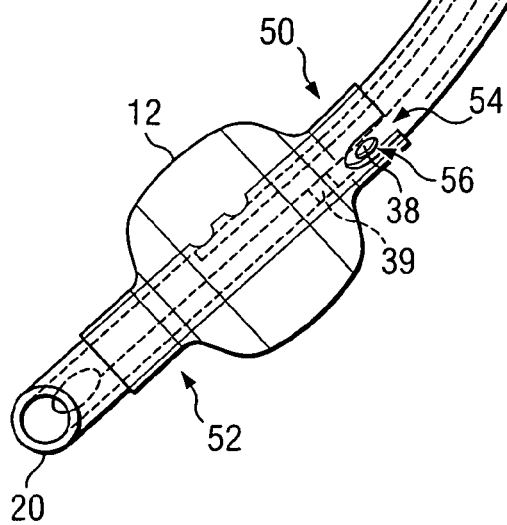

Turning now to the drawings, FIG. 1 illustrates an example medical tube 10 including an inflatable cuff 12 having a notched collar, in accordance with an example embodiment of the disclosure. Tube 10 may include a tubular body 16 having an open proximal end 18 and an open distal end 20. Tubular body 16 may define a gas-conveying passageway 22 for mechanical ventilation of a subject. Proximal end 18 may include a connector 24 configured for attachment to a mechanical ventilator (not shown).

During intubation of tube 10, cuff 12 may be at least partially collapsed. Once properly in place, cuff 12 may be inflated via an inflation lumen 30 formed in or otherwise associated with tubular body 16. Inflation lumen 30 may be coupled to an inflation line 32 terminating in a fixture 34 that allows inflation of cuff 12 via inflation lumen 30.

Tubular body 16 may also include a suction lumen 36 formed in or otherwise associated with tubular body 16. Suction lumen 36 may include an opening 38 extending through the wall of tubular body 16 through which secretions or other matter accumulated on or proximate cuff 12 may be removed. In this embodiment, suction lumen 36 extends to the distal end 20 of tubular body 16 and includes a sealing plug 39. In other embodiments, suction lumen 36 may terminate before the distal end 20 of tubular body 16 (e.g., just beyond opening 38) or may terminate at opening 38. As shown, an exterior suction tube 40 may be communicatively coupled to lumen 36 for removing secretions or other matter through opening 38, as discussed below in greater detail. Suction tube 40 may include an end fixture 42 including a cap 44.

Inflatable cuff 12 may be mounted on tubular body 16 adjacent distal end 20 of tubular body 16. Cuff 12 may be mounted on tubular body 16 by one or more collars and/or other suitable means. In the example embodiment shown in FIG. 1, cuff 12 may be mounted on tubular body 16 by a first collar 50 and a second collar 52. First collar 50 may include a notch 54 positioned relative to opening 38 in tubular body 16 such that a passageway 56 extends through at least a portion of notch 54 and at least a portion of opening 38. Passageway 56 may provide a path for secretions or other matter proximate cuff 12 to flow into suction lumen 36 for removal. As used herein, a "notch" may refer to any hole, opening, or cutout, which may have any suitable configuration or shape (e.g., U-shaped, V-shaped, arc-shaped, circular, elliptical, ovoid, square, rectangular, octagonal, hexagonal, etc.), may be open-ended (e.g., an open-ended cutout from an edge of first collar 50) or enclosed (e.g., a hole), and may be formed in any suitable manner before, after, or during the mounting of cuff 12 on tubular body 16.

Cuff 12 may comprise any type of inflatable cuff. For example, cuff 12 may be a high volume, low pressure cuff; a low volume, high pressure cuff; or a low volume, low pressure cuff. Cuff 12 may have any suitable shape, size, and/or configuration, and may be formed from any one or more materials. For example, cuff 12 may be manufactured from any suitable polymeric or other material, e.g., PVC (polyvinyl chloride), polyurethane, polyisoprene, and/or silicone.

To insert and/or position tube 10 in the trachea, tube 10 may be inserted down the trachea to a point just above (e.g., about 3 cm above) the carina. Cuff 12 may then be inflated by pumping air into cuff 12 through inflation line 32 and inflation lumen 30. Typically, inflation air may be provided by a syringe inserted into fixture 34. In some situations, inflation of cuff 12 to a pressure of 25-30 cm $H_2O$ (or any other clinically appropriate pressure level) may act to seal cuff 12 against the inner wall of the trachea, thus effectively sealing the trachea to prevent gas (e.g., gas pumped into the lungs through tube 10) from backing up around tube 10. Additionally, or alternatively, cuff 12 may act to secure or position tube 16 within the trachea.

Proximal end 18 of tubular body 16 may be attached to a ventilator using connector 24 for mechanical ventilation of the subject. Following intubation, fluid secretions and/or other matter may accumulate near the proximal end of cuff 12. These secretions may carry bacteria or other pathogens in an environment suitable for pathogen growth. Accordingly, the secretions may be periodically or continuously removed through passageway 56, lumen 36, and suction tube 40. Cap 44 may be removed and fixture 42 may be connected to a suction machine (not shown) for removing the secretions; alternately, a syringe may be used for this purpose.

Figure 2A:
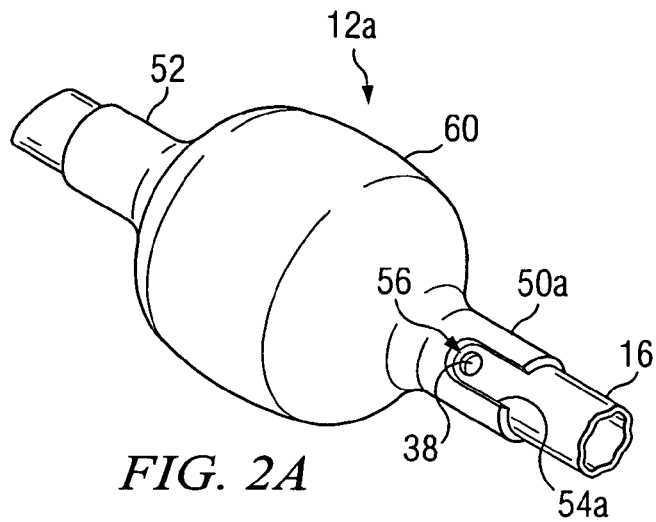
FIGS. 2A-2C are enlarged views of inflatable cuffs having notched collars, in accordance with various example embodiments of the disclosure.
Figure 2B:
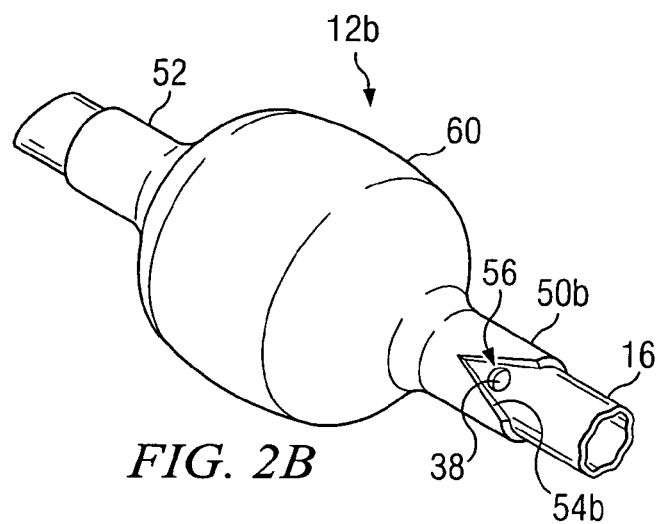
Figure 2C:
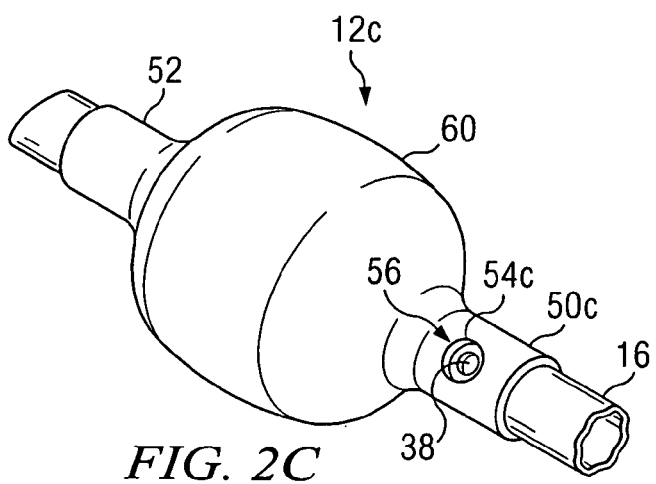

FIGS. 2A-2C are enlarged views of cuffs 12 having a notched collar 50, in accordance with various example embodiments of the disclosure. In each embodiment, cuff 12 is shown in its inflated state with collars 50 and 52 at respective ends of cuff 12 for attaching cuff 12 to tubular body 16 having a suction opening 38. Collar 50 may include a notch 54 positioned relative to opening 38 such that passageway 56 extends through at least a portion of notch 54 and at least a portion of opening 38, such that secretions or other matter may flow into suction lumen 36 through passageway 56.

For example, FIG. 2A illustrates a cuff 12a including a collar 50a having a notch 54a that is generally U-shaped and open-ended.

As another example, FIG. 2B illustrates a cuff 12b including a collar 50b having a notch 54b that is generally V-shaped and open-ended.

As another example, FIG. 2C illustrates a cuff 12c including a collar 50c having a notch 54c that is an enclosed hole. Hole 54c may have any suitable shape and/or size relative to opening 38. For example, in some embodiments (e.g., where hole 54c is formed before mounting cuff 12c on tubular body 16), hole 54c may be larger than opening 38, e.g., to facilitate the alignment of hole 54c with opening 38 to form passageway 56. In other embodiments (e.g., where hole 54c is formed after cuff 12c is mounted on tubular body 16), hole 54c may have the same size and shape as opening 38. In other embodiments, hole 54c may be smaller than opening 38.

The embodiments shown in FIGS. 2A-2C are examples only. As discussed above, notch 54 may refer to any hole, opening, or cutout, which may have any suitable configuration or shape (e.g., U-shaped, V-shaped, arc-shaped, circular, elliptical, ovoid, square, rectangular, octagonal, hexagonal, etc.), may be open-ended (e.g., an open-ended cutout from an edge of first collar 50) or enclosed (e.g., a hole), and may be formed in any suitable manner before, after, or during the mounting of cuff 12 on tubular body 16.

In some embodiments, notch 54 may allow suction opening 38 to be positioned in close proximity to an inflatable portion 60 of cuff 12 and/or to a transition between collar 50 and inflatable portion 60 of cuff 12. Such positioning may facilitate the removal of secretions or other matter that may collect near inflatable portion 60 and/or the transition between collar 50 and inflatable portion 60 through passageway 56.

Collars 50 and 52 may be elastically stretched around tubular body 16, which may substantially secure collars 50 and 52 to tubular body 16. In some embodiments, all or portions of collars 50 and/or 52 may be bonded to tubular body 16 in any suitable manner. For example, in one embodiment, collars 50 and/or 52 may be bonded to an outer surface of tubular body 16 using a cyclohexanome solvent bond that may dissolve portions of collar 50/52 and tubular body 16 such that the surfaces of each become intermingled.

Figure 3A:
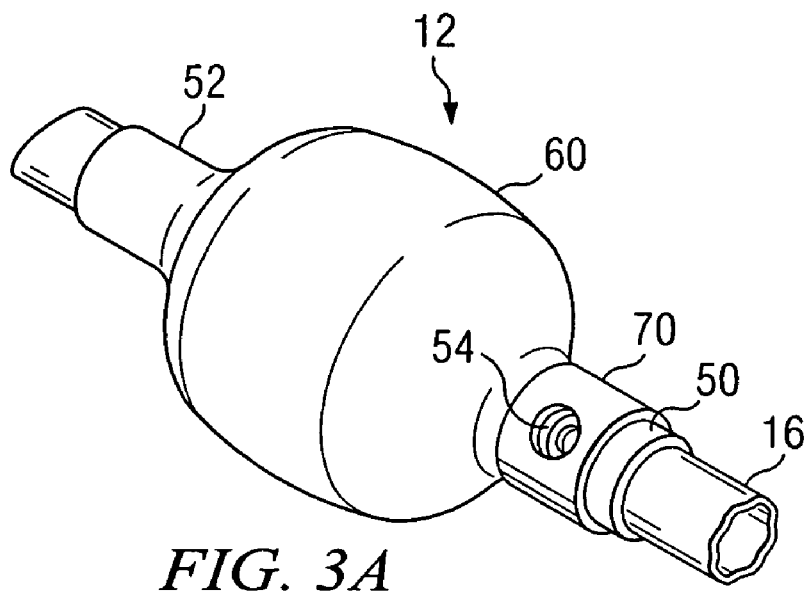
FIGS. 3A-3B illustrate inflatable cuffs having bands used to help secure a cuff collar to a tubular body, in accordance with example embodiments of the disclosure.

As another example, a band or ring 70 may be positioned around collar 50 to secure or help secure collar 50 to tubular body 16. In some embodiments, all or a portion of notch 54 extends through band 70. For example, FIG. 3A illustrates an example embodiment in which a band 70 extends around collar 50 and notch 54 extends through band 70 such that passageway 56 extends through band 70, collar 50, and tubular body 16. In other embodiments, notch 54 does not extend through band 70. For example, FIG. 3B illustrates an example embodiment in which a band 70 extends around collar 50 but notch 54 does not extend through band 70.

Band 70 may have any suitable shape, size, and/or thickness, and may be located at any position along the length of collar 50 relative to notch 54. Band 70 may be made from the same material as cuff 12 or from any other suitable material. Band 70 may be secured to or around collar 50 in any suitable manner. For example, band 70 may be an elastic band secured around collar 50 by elastic forces. As another example, band 70 may coupled to collar 50 using any suitable heat treatment (e.g., using RF, hot air, or ultrasonic techniques). As another example, band 70 may be secured to or bonded with collar 50 using a solvent.

In some embodiments, a second band, which may or may not be similar to band 70, may be positioned around collar 52 to secure or help secure collar 52 to tubular body 16.

Figure 3B:
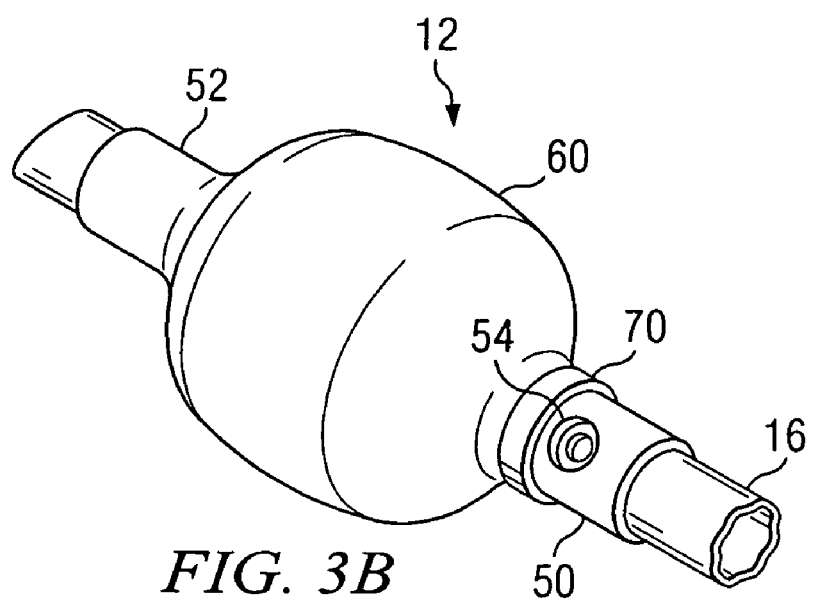

In some embodiments, e.g., the embodiment shown in FIG. 3B, band 70 may act as a spacer to help prevent opening 38 from contacting and becoming occluded by the tracheal wall (during suctioning or otherwise), which occlusion may cause irritation and/or rubbing of the tracheal wall that can result in inflammation, scarring, stenosis, and/or have other undesirable effects. Alternatively, or in addition to band 70, one or more spacers may be provided on cuff 12 and or tubular body 16 to help prevent opening 38 from becoming occluded. For example, one or more spacing members may be formed integral to, or coupled to, inflatable portion 60 and/or collar 50 to help prevent the occlusion of opening 38. As another example, one or more spacing members may be formed integral to, or coupled to, tubular body 16 to help prevent the occlusion of opening 38. For instance, in some embodiments, tubular body 16 may include one or more projections located proximate opening 38, e.g., as described in co-pending PCT Application No. PCT/US2005/016577, filed May 11, 2005.

Figure 4A:
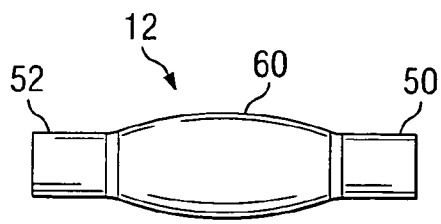
FIGS. 4A-4E illustrate an example method of attaching an inflatable cuff having a notched collar to a tubular body of a medical tube, in accordance with one embodiment of the disclosure.
Figure 4B:
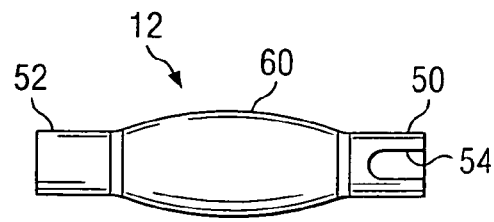

FIGS. 4A through 4E illustrate an example method of attaching a cuff 12 having a notched collar 50 to a tubular body 16 of an endotracheal tube, in accordance with one embodiment of the disclosure. FIG. 4A shows cuff 12, which may include inflatable portion 60 and collars 50 and 52 at respective ends of cuff 12. As shown in FIG. 4B, a notch 54 may be formed in collar 50. As discussed above, notch 54 may have any suitable shape, size, and/or configuration, and may be formed in any suitable manner.

Figure 4C:
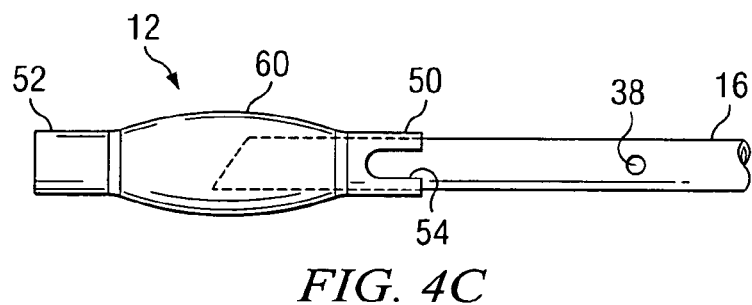
Figure 4D:
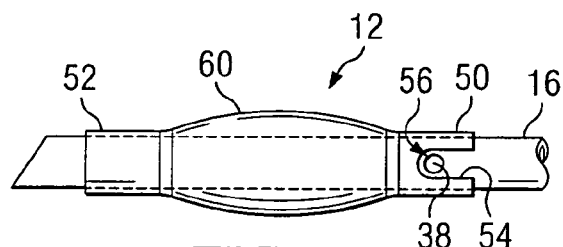

As shown in FIG. 4C, cuff 12 with notched collar 50 may be mounted on tubular body 16. Cuff 12 may be mounted on tubular body 16 in any suitable manner, e.g., by manually or automatically inserting an end of tubular body 16 through the openings defined by collars 50 and 52, or in any other suitable manner. As shown in FIG. 4D, cuff 12 may be positioned on tubular body 16 such that notch 54 is positioned relative to opening 38 to define passageway 56 extending through both notch 54 and opening 38. In addition, cuff 12 may be positioned on tubular body 16 such that suction opening 38 is positioned proximate inflatable portion 60 of cuff 12.

Figure 4E:
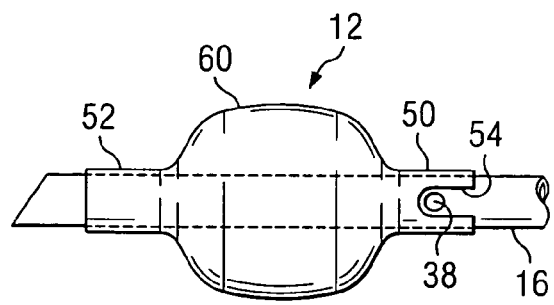

FIG. 4E shows cuff 12, having been mounted on tubular body 16 as shown in FIGS. 4A-4D, in an inflated state. In this example embodiment, collars 50 and 52 are secured to tubular body 16 such that collars 50 and 52 do not inflate, while inflatable portion 60 inflates outwardly. Collars 50 and/or 52 may be secured to tubular body 16 in any suitable manner, e.g., by being elastically stretched around tubular body 16 and/or by being permanently secured by solvent bond, heat treatment (e.g., using RF, hot air, or ultrasonic techniques) or in any other manner.

FIGS. 5A-5E illustrate an example method of mounting an inflatable cuff 12 on a tubular body 16 of a medical tube and forming a notch 54 in the cuff 12 and an opening 38 in the tubular body 16, in accordance with one embodiment of the disclosure.

Figure 5A:
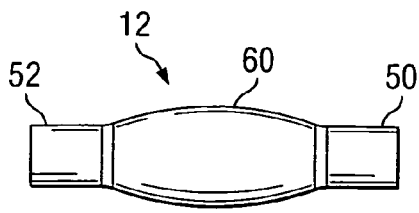
FIGS. 5A-5E illustrate an example method of mounting an inflatable cuff on a tubular body of a medical tube and forming a notch in the cuff and an opening in the tubular body, in accordance with one embodiment of the disclosure.
Figure 5B:
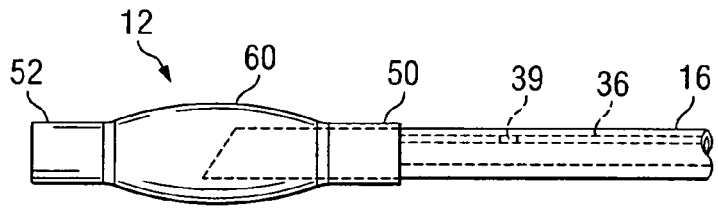
Figure 5C:
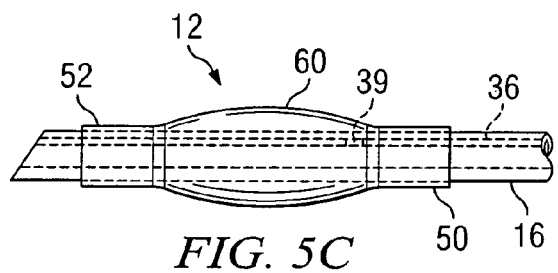

FIG. 5A shows cuff 12, which may include inflatable portion 60 and collars 50 and 52 at respective ends of cuff 12. As shown in FIG. 5B, cuff 12 may be mounted on tubular body 16. Cuff 12 may be mounted on tubular body 16 in any suitable manner, e.g., by manually or automatically inserting an end of tubular body 16 through the openings defined by collars 50 and 52, or in any other suitable manner. As shown in FIG. 5C, cuff 12 may be positioned on tubular body 16 such that collar 50 overlies an area of tubular body 16 through which an opening 38 may be suitably formed. For example, cuff 12 may be appropriately positioned relative to sealing plug 39 located in suction lumen 36 (discussed above with reference to FIG. 1). In some embodiments, collars 50 and/or 52 may be bonded to tubular body 12, e.g., as described above with reference to FIG. 4D.

Figure 5D:
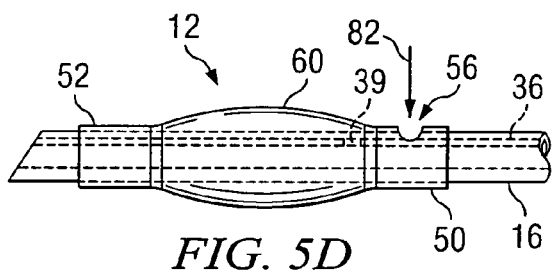

Once cuff 12 is positioned and/or bonded to tubular body 16, notch 54 and opening 38 may be formed in collar 50 and tubular body 16, respectively, in any suitable manner, thereby forming passageway 56. For example, in some embodiments, as shown in FIG. 5D, notch 54 and opening 38 (and thus passageway 56) may be formed by cutting (e.g., by punching, drilling, or otherwise cutting) across a side of tubular body 16, in a direction perpendicular to the page with reference to FIG. 5D (i.e., in the direction indicated by arrow 80 in FIG. 5E). In some embodiments, such cutting may form a circular or ovoid notch 54 and a circular or ovoid opening 38. In other embodiments, notch 54 and opening 38 (and thus passageway 56) may be formed by cutting (e.g., by punching, drilling, or otherwise cutting) perpendicularly through a side of collar 50 and tubular body 16 (i.e., in a direction indicated by arrow 82 in FIG. 5D).

Thus, notch 54 and opening 38 may be formed substantially simultaneously by cutting (e.g., punching, drilling, or otherwise cutting) through both collar 50 and tubular body 16. However, in other embodiments, notch 54 and opening 38 may not be formed substantially simultaneously. For example, notch 54 and opening 38 may be formed by separate cutting processes.

Figure 5E:
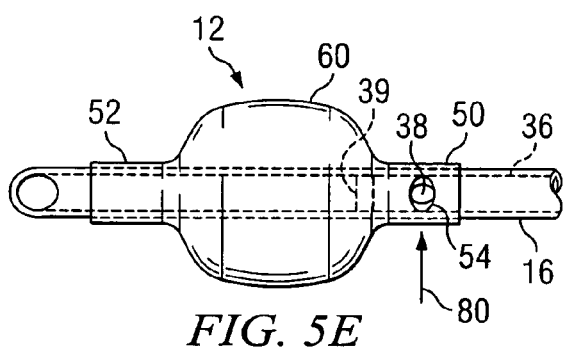

FIG. 5E illustrates cuff 12 rotated 90 degrees from the views of FIGS. 5A-5D, in order to illustrate a top view of notch 54 and opening 38. In this example embodiment, one or both of notch 54 and opening 38 may have an ovoid shape, which may result from the cross-cutting process discussed above (i.e., cutting in the direction indicated by arrow 82). In addition, cuff 12 is shown in FIG. 5E in an inflated state.

In some embodiments (e.g., where a single cutting process using a single bit or punch member is used to form both notch 54 and opening 38), notch 54 and opening 38 may have the same size and shape. In other embodiments (e.g., where multiple cutting processes are used to form notch 54 and opening 38, or where a dual-diameter bit or punch member is used to form notch 54 and opening 38), notch 54 may have a different shape and/or size than opening 38.

As discussed above, passageway 56 may extends through at least a portion of notch 54 and at least a portion of opening 38. Notch 54 may be partially or fully aligned with opening 38. Notch 54 may be said to be fully aligned with opening 38 if either (a) none of notch 54 directly overlies a material (i.e., non-opening) portion of tubular body 16, or (b) none of opening 38 directly underlies a material (i.e., non-notch) portion of collar 50. Notch 54 may be said to be partially aligned with opening 38 if both (a) a portion of notch 54 directly overlies a material (i.e., non-opening) portion of tubular body 16, and (b) a portion of opening 38 directly underlies a material (i.e., non-notch) portion of collar 50.

According to another embodiment, a method of forming notch 54 may include mounting a cuff 12 having no notched cuff portion 54 on a tubular body 16 that already includes an opening 38. Cuff 12 may be positioned on tubular body 16 such that collar 50 is aligned over opening 38. Once cuff 12 is appropriately positioned, notch 54 may be formed in collar 50 (e.g., by any suitable cutting process) such that a passageway 56 extends through at least a portion of notch 54 and at least a portion of opening 38 for removing secretions or other matter proximate cuff 12.

Figure 6:
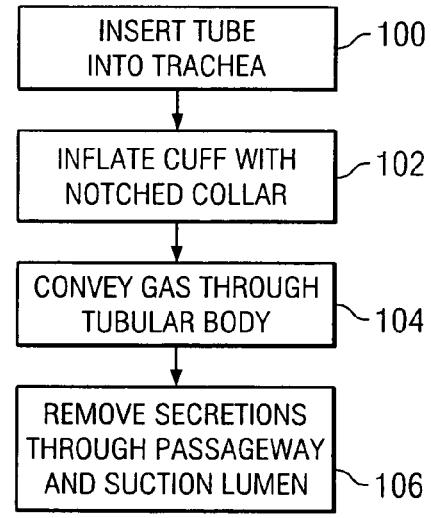
FIG. 6 is a flow diagram of a method of intubation of a medical tube having a cuff with a notched collar, in accordance with one embodiment of the disclosure.

FIG. 6 is a flow diagram of a method of intubation of a tube having a cuff with a notched collar, in accordance with one embodiment of the disclosure. At step 100, a tube may be inserted into a subject's trachea. The tube may have a tubular body and an inflatable cuff having a notched collar positioned over a suction opening in the tubular body to form a secretion-removal passageway for removal of secretions or other matter via a suction lumen. The tube may have any suitable additional features, e.g., a Magill curve to facilitate intubation. At step 102 the inflatable cuff may be inflated to seal, secure, and/or position the tubular body against the tracheal wall. At step 104, gas may be conveyed (e.g., from a gas source) through the tubular body to an area of the subject's body (e.g., the lungs). At step 106, secretions or other matter proximate the inflatable cuff may be removed by suction through the secretion-removal passageway and suction lumen.

The order of the steps discussed above can vary according to various embodiments. For example in some embodiments, gas may be conveyed through the tubular body prior to sealing/securing the tube to the tracheal wall using the inflatable cuff.

Figure 7A:
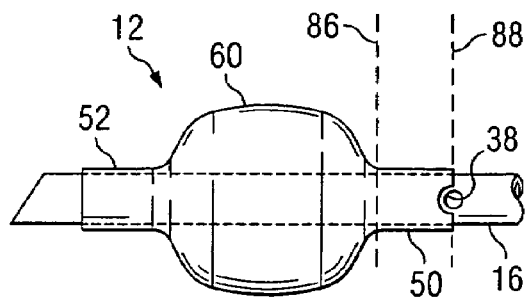
FIGS. 7A-7B illustrate various locations of a suction opening formed in a tubular body of a medical tube relative to an inflatable cuff mounted on the tubular body, according to example embodiments.
Figure 7B:
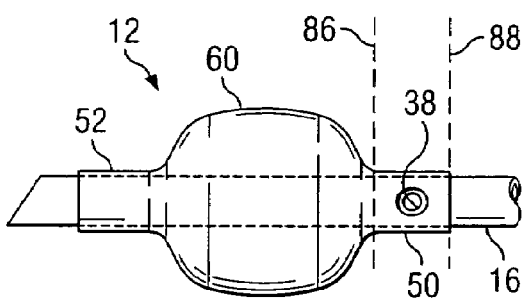

FIGS. 7A-7B illustrate various locations of opening 38 relative to cuff 12, according to example embodiments. Opening 38 may be located in any suitable location relative to collar 50 and/or inflatable portion 60 of cuff 12. For example, at least a portion of opening 38 may be located at any position along a length extending from a first end 86 of collar 50 to a second end 88 of collar 50. First end 86 of collar 50 may be located at or proximate a transition between collar 50 and inflatable portion 60.

Figure 8A:
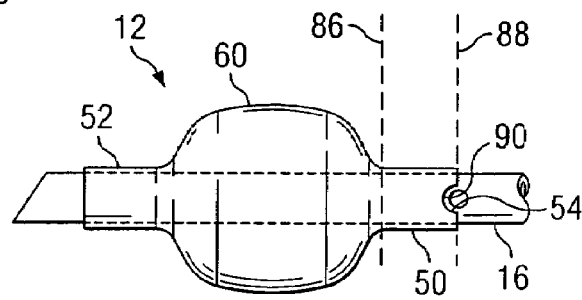
FIGS. 8A-8B illustrate various locations of an open-ended notch formed in an inflatable cuff mounted on a medical tube, according to example embodiments.
Figure 8B:
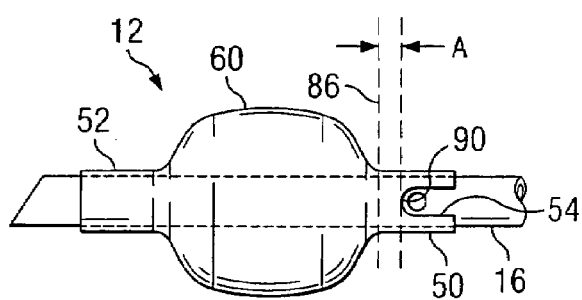

FIGS. 8A-8B illustrate various locations of an open-ended notch 54, according to example embodiments. Open-ended notch 54 may be located in any suitable location on collar 50. For example, a first end 90 of notch 54 closest to inflatable portion 60 may be located at any position along a length extending from first end 86 of collar 50 to second end 88 of collar 50. In some embodiments, first end 90 of notch 54 may be spaced sufficiently apart from first end 86 of collar 50 to provide sufficient material around collar 50 for securing collar 50 to tubular body 16. For example, as shown in FIG. 8B, first end 90 of notch 54 may be spaced sufficiently apart from first end 86 of collar 50, indicated as distance A, to provide sufficient material around collar 50 for securing collar 50 to tubular body 16. For example, in some embodiments, distance A may be at least 0.050 inches. In one embodiment, distance A may be about 0.0625 inches.

Figure 9:
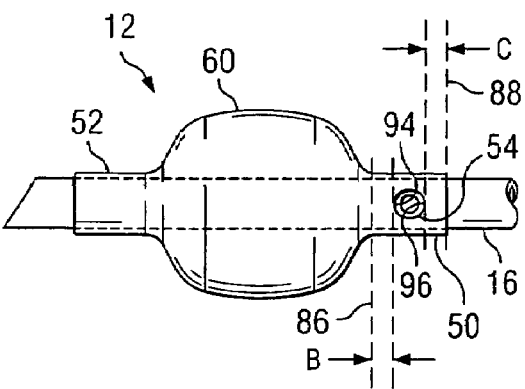
FIG. 9 illustrates the positioning of an enclosed notch formed in a collar of an inflatable cuff mounted on a medical tube, according to an example embodiment.

FIG. 9 illustrates the positioning of an enclosed notch 54 formed in collar 50, according to an example embodiment. Enclosed notch 54 may be located in any suitable location on collar 50. In some embodiments, notch 54 may be spaced sufficiently apart from first end 86 and/or second end 88 of collar 50 to provide sufficient material on one or both sides of notch 54 for securing collar 50 to tubular body 16.

For example, as shown in FIG. 9, a first end 94 of notch 54 may be spaced sufficiently apart from first end 86 of collar 50, indicated as distance B, to provide sufficient material around collar 50 for securing collar 50 to tubular body 16. In some embodiments, distance B may be at least 0.050 inches. In one embodiment, distance B may be about 0.0625 inches.

As another example, a second end 96 of notch 54 may be spaced sufficiently apart from second end 88 of collar 50, indicated as distance C, to provide sufficient material around collar 50 for securing collar 50 to tubular body 16. In some embodiments, distance C may be at least 0.050 inches. In one embodiment, distance C may be about 0.0625 inches.

It will be appreciated that while the disclosure is particularly described in the context of endotracheal tubes, the apparatuses, techniques, and methods disclosed herein may be similarly applied in other contexts. For example, similar principles may be applied to a variety of other surgical and/or medical tubes having inflatable cuffs, e.g., tracheostomy tubes, oropharyngeal tubes, or other medical tubes or catheters. Additionally, it should be understood that various changes, substitutions and alterations can be made herein without departing from the spirit and scope of the disclosure as illustrated by the following claims.

What is claimed is:

1. A medical device, comprising:
  a tubular body configured to communicate gas, the tubular body including an opening; a suction lumen extending along at least a portion of the tubular body and in fluid communication with the opening in the tubular body; and
  an inflatable cuff coupled to the tubular body at least by a collar;
  wherein said collar includes a notch positioned relative to the opening in the tubular body such that a passageway extends through at least a portion of the notch and at least a portion of the opening.

2. A medical device according to claim 1, wherein:
  the inflatable cuff includes another collar; and
  the inflatable cuff is coupled to the tubular body at least by the two collars.

3. A medical device according to claim 1, wherein the notch and the opening are fully aligned.

4. A medical device according to claim 1, wherein the notch and the opening are partially aligned such that at least a portion of the notch overlies a material portion of the tubular body and at least a portion of the opening underlies a material portion of the collar.

5. A medical device according to claim 1, wherein:
  the inflatable cuff includes an inflatable portion;
  the collar has a first end adjacent the inflatable cuff and a second end; and
  an edge of the notch closest to the second end of the collar is at least 0.05 inches from the second end of the collar.

6. A medical device according to claim 5, wherein the edge of the notch closest to the second end of the collar is about 0.0625 inches from the second end of the collar.

7. A medical device according to claim 1, wherein:
the inflatable cuff includes an inflatable portion adjacent a first end of the collar; and
an edge of the notch closest to the first end of the collar is at least 0.05 inches from the first end of the collar.

8. A medical device according to claim 7, wherein the edge of the notch closest to the first end of the collar is about 0.0625 inches from the first end of the collar.

9. A medical device according to claim 1, further comprising a band extending at least partially around the collar to help secure the collar to the tubular body.

10. A medical device according to claim 1, wherein the notch is open-ended.

11. A medical device according to claim 1, wherein the notch comprises an enclosed hole.

12. A medical device according to claim 1, wherein the notch is substantially V-shaped.

13. A medical device according to claim 1, wherein the notch is substantially U-shaped.

14. A medical device according to claim 1, wherein the notch has a substantially rectangular shape.

15. A medical device according to claim 1, wherein the notch has a substantially square shape.

16. A medical device according to claim 1, wherein the notch has a substantially circular shape.

17. A medical device according to claim 1, wherein the notch has a substantially ovoid shape.

18. A medical device according to claim 1, wherein the notch has a substantially elliptical shape.

19. A medical device according to claim 1, wherein the notch in the collar and the opening in the tubular body have substantially similar shapes.

20. A medical device according to claim 1, wherein the notch in the collar and the opening in the tubular body have different shapes.

21. A medical device according to claim 1, wherein the notch in the collar and the opening in the tubular body have substantially similar sizes.

22. A medical device according to claim 1, wherein the notch in the collar and the opening in the tubular body have different sizes.

23. A medical device according to claim 1, wherein the medical device comprises an endotracheal tube.

24. A medical device according to claim 1, wherein the medical device comprises a tracheostomy tube.

25. A medical device according to claim 1, wherein the medical device comprises an oropharyngeal tube.

26. A medical device according to claim 1, wherein the medical device comprises a catheter.

27. A medical device, comprising:
conveying means for channeling gas to an area of the body including an opening; a suction lumen extending along at least a portion of the conveying means and in fluid communication with the opening in the conveying means;
sealing means for sealing said conveying means against the wall of a body cavity; and
attaching means for attaching said sealing means to said conveying means, wherein the attaching means includes a collar having a notch positioned relative to the opening in the conveying means such that a passageway extends through at least a portion of the notch and at least a portion of the opening.

* * * * *